(12) United States Patent
Park et al.

(10) Patent No.: US 7,265,224 B2
(45) Date of Patent: Sep. 4, 2007

(54) RED LUMINESCENT COMPOUND AND ORGANIC ELECTROLUMINESCENT DEVICE USING THE SAME

(75) Inventors: Soo-Jin Park, Seoul (KR); Kwan-Hee Lee, Seoul (KR); Jae-Il Kim, Seoul (KR); Jin-Kyu Lee, Seoul (KR); Jang-Hyuk Kwon, Suwon (KR)

(73) Assignee: Samsung SDI Co., Ltd., Suwon-si, Gyeonggi-do (KR)

( * ) Notice: Subject to any disclaimer, the term of this patent is extended or adjusted under 35 U.S.C. 154(b) by 0 days.

(21) Appl. No.: 10/733,636

(22) Filed: Dec. 12, 2003

(65) Prior Publication Data

US 2004/0127710 A1 Jul. 1, 2004

(30) Foreign Application Priority Data

Dec. 28, 2002 (KR) .................. 10-2002-0085904

(51) Int. Cl.
*C07F 13/00* (2006.01)
*C07F 17/02* (2006.01)
*H01L 51/54* (2006.01)

(52) U.S. Cl. .................. 546/2; 428/690; 428/917; 313/504

(58) Field of Classification Search .................. 546/2; 428/690, 917; 313/504
See application file for complete search history.

(56) References Cited

U.S. PATENT DOCUMENTS

| 2001/0019782 A1 | 9/2001 | Igarashi et al. |
| 2002/0034656 A1 | 3/2002 | Thompson et al. |
| 2002/0121638 A1 | 9/2002 | Grushin et al. |

FOREIGN PATENT DOCUMENTS

| JP | 2001-345183 | 12/2001 |
| KR | 2002-0086950 | 11/2002 |

OTHER PUBLICATIONS

Korean Office Action dated Jan. 15, 2005 for KR2002-0085904.
Chinese Office Action No. CPCH03635643; dated Feb. 4, 2005 for Patent Application No. 200310121683; corresponds to U.S. Appl. No. 10/733,636 (current application).

*Primary Examiner*—Rita Desai
(74) *Attorney, Agent, or Firm*—Robert E. Bushnell, Esq.

(57) ABSTRACT

A novel phosphorescent material containing an iridium metal compound and an organic electroluminescent device using the same are provided. When used for an emissive layer of an organic electroluminescent device, the phosphorescent material offers greater luminescent efficiency and improved driving voltage characteristics, compared to conventional red luminescent materials, and reduces the amount of power consumed in the organic electroluminescent device.

7 Claims, 10 Drawing Sheets

| RED PL COMPOUND | | |
|---|---|---|
| Dye | $\lambda_{max}$/nm | $\Phi_{phos}$ |
| $pq_2$Ir(acac) | 590 | 0.10 |
| $pq_2$Ir(tmd) | 593 | 0.10 |
| $pq_2$Ir(L-pro) | 590 | 0.15 |
| $pq_2$Ir(pic) | 571 | 0.27 |
| $pq_2$Ir(quin) | 571 | 0.28 |
| $pq_2$Ir(oppz) | 590 | 0.17 |

RED LUMINESCENT COMPOUND AND ORGANIC ELECTROLUMINESCENT DEVICE USING THE SAME

CLAIM OF PRIORITY

This application claims the priority of Korean Patent Application No. 2002-85904, filed on Dec. 28, 2002, in the Korean Intellectual Property Office, the disclosure of which is incorporated herein in its entirety by reference.

BACKGROUND OF THE INVENTION

1. Field of the Invention

The present invention relates to a red luminescent compound and an organic electroluminescent device using the same, and more particularly, to a red luminescent compound and an organic electroluminescent device using the same that offers improved luminescent efficiency and driving voltage characteristics.

2. Description of the Related Art

Electroluminescent (EL) devices known as a self-luminous display have the advantages of large viewing angle, high contrast property, and short response time.

EL devices can be classified depending on the material composing their emissive layer into inorganic EL devices and organic EL devices. Organic EL devices have the advantages of higher luminance, lower driving voltage, shorter response time, and the ability to display a wider range of colors, over inorganic EL devices.

A general organic EL device includes an anode on the top surface of a substrate, with a hole transporting layer, an emissive layer, an electron transporting layer, and a cathode formed in sequence on the anode, wherein the hole transporting layer, the emissive layer, and the electron transporting layer are thin films made of organic compounds.

Organic EL devices having such a structure described above operate according to the following principles.

When a voltage is applied across the anode and the cathode, holes injected from the anode migrate via the hole transporting layer into the emissive layer. Electrons injected from the cathode migrate via the electron transporting layer into the emissive layer and combine with the holes therein to generate excitons. When the excitons transit from excited state to base state, molecules of the emissive layer emit light to form visible images.

Materials for the emissive layer can be classified depending on their light emission mechanism, into fluorescent materials that emit light from excitons in a singlet state and phosphorescent materials that emit light from excitons in a triplet state.

In general, phosphorescent materials are organometallic compounds containing a heavy atom and an organic ligand. In phosphorescence from phosphorescent materials, excitons in a non-emissive triplet state due to the heavy atom participate in emission via transition. Such phosphorescent materials use 75% of triplet state excitons for emission and offers higher luminescent efficiency compared to fluorescent materials using only 25% of singlet state excitons for emission.

Red luminescent materials, for example, DCJTB(4-(di-cyanomethylene)-2-t-butyl-6-(1,1,7,7-tetramethyljulolidyl-9-enyl)-4H-pyran), have been developed. However, currently available red luminescent materials offer low luminescent efficiency and poor color purity.

Recently, research on phosphorescent materials including a second dopant such as rubrene or including an iridium metallic compound has conducted, as disclosed in U.S. 2002/0,121,638A1 and U.S. 2002/0,034,656 A1. However, these compounds still require improvements in luminescent efficiency and film stability.

Therefore, there is a need for the development of new red luminescent compounds applicable to red EL devices or full-color light emitting devices.

SUMMARY OF THE INVENTION

It is therefore an object of the present invention to provide a red luminescent compound with improved luminescent efficiency, an organic electroluminescent device and an image display using the red luminescent compound.

In order to achieve the above objectives, in accordance with an aspect of the present invention, there is provided a compound having the formula (1) below:

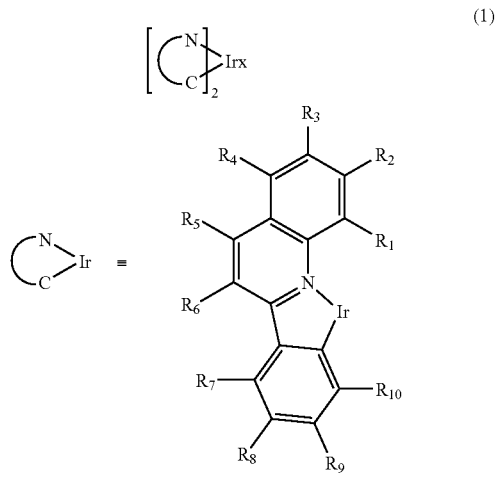

(1)

where $R_1$, $R_2$, $R_3$, $R_4$, $R_5$, $R_6$, $R_7$, $R_8$, $R_9$, and $R_{10}$ are independently selected from the group consisting of hydrogen, a substituted or unsubstituted C1-C30 alkyl group, a substituted or unsubstituted C2-C20 alkenyl group, a substituted or unsubstituted C1-C20 alkoxy group, a substituted or unsubstituted C6-C30 aryl group, a substituted or unsubstituted C6-C30 fused aromatic ring, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C2-C20 heterocycloalkyl group, a halogen atom, and a cyano group, and X is a bidentate ligand.

In according to another aspect of the present invention, there is provided an organic EL device using the red luminescent compound of formula (1) above. An organic EL device according to the present invention may include an organic layer, which includes the compound having the formula (1), between a pair of electrodes.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
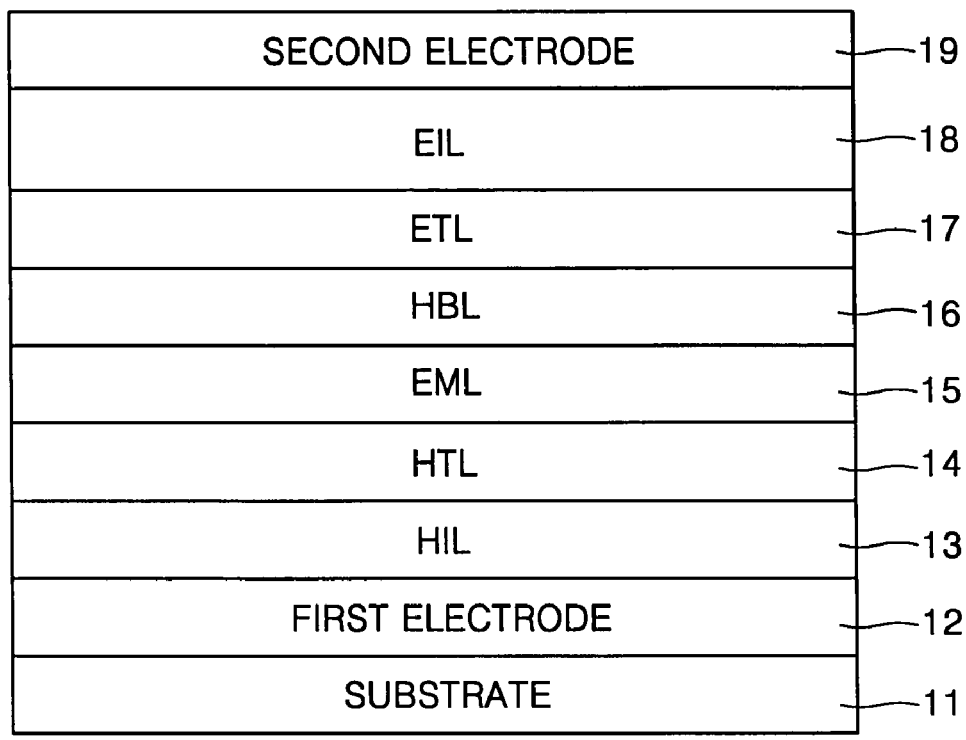
FIG. 1 is a sectional view illustrating the structure of a general organic electroluminescent (EL) device.
Figure 2:
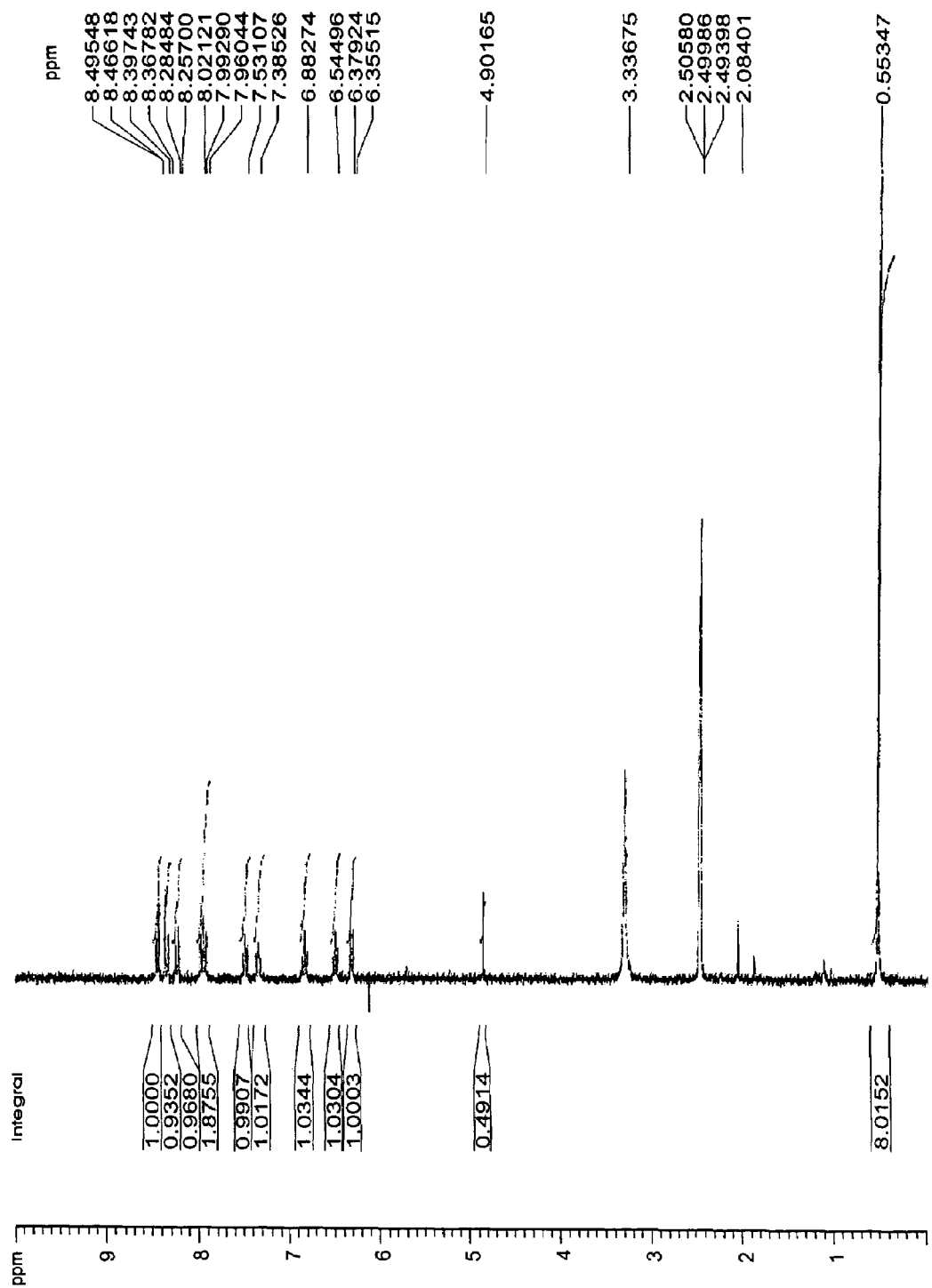
FIG. 2 shows the nuclear magnetic resonance (NMR) spectrum of a compound of formula (2) according to the present invention.
Figure 3:
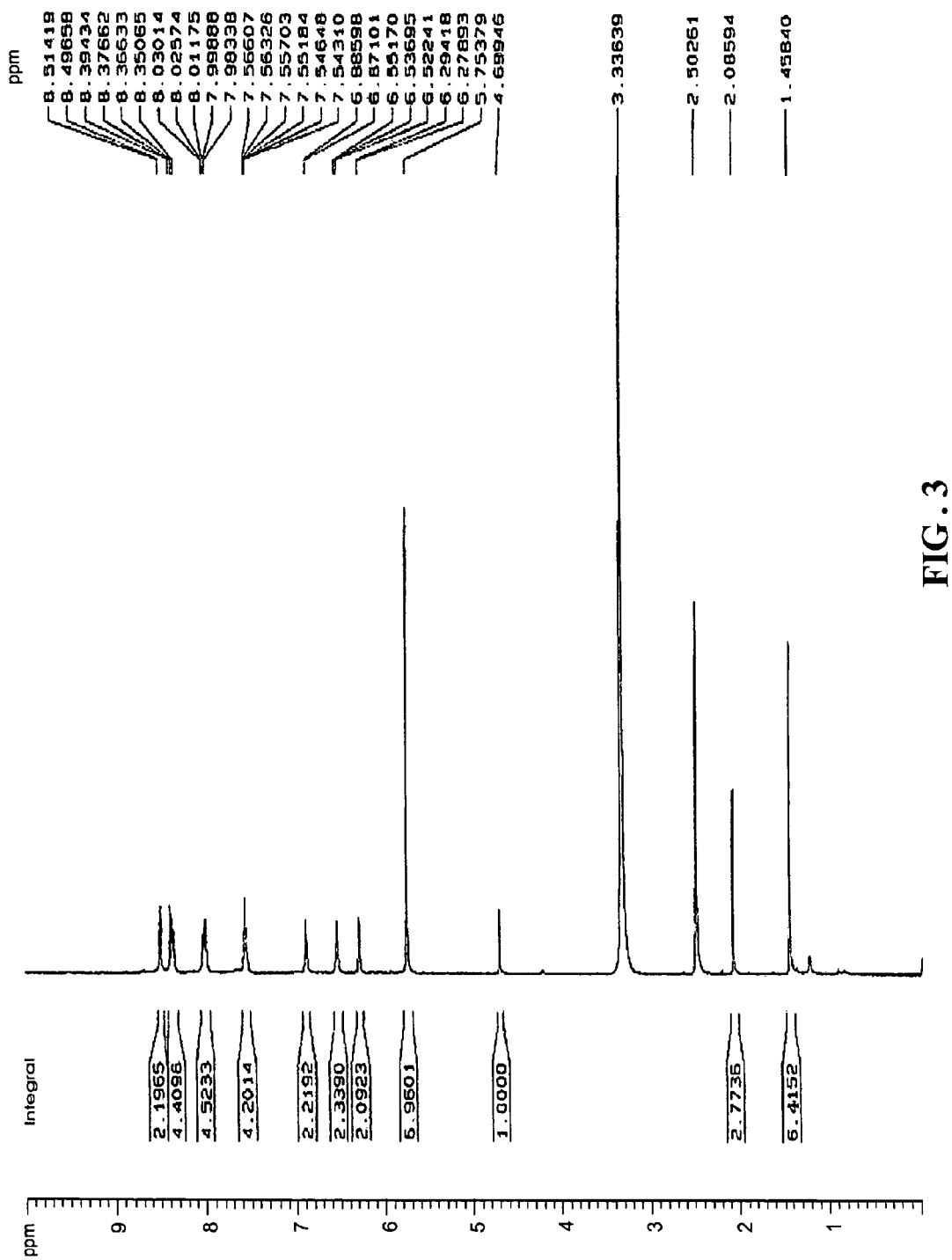
FIG. 3 shows the NMR spectrum of a compound of formula (3) according to the present invention.
Figure 4:
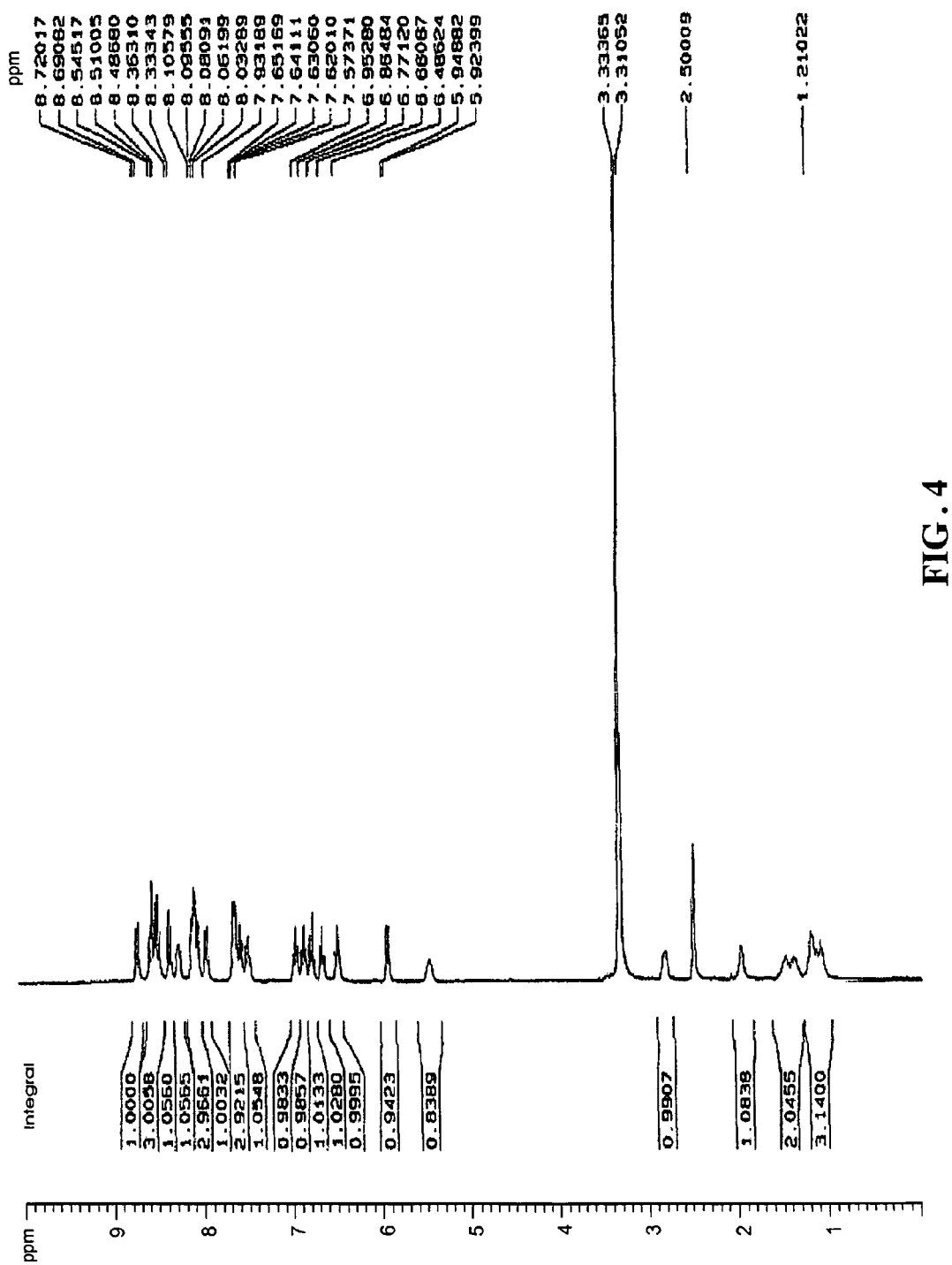
FIG. 4 shows the NMR spectrum of a compound of formula (4) according to the present invention.
Figure 5:
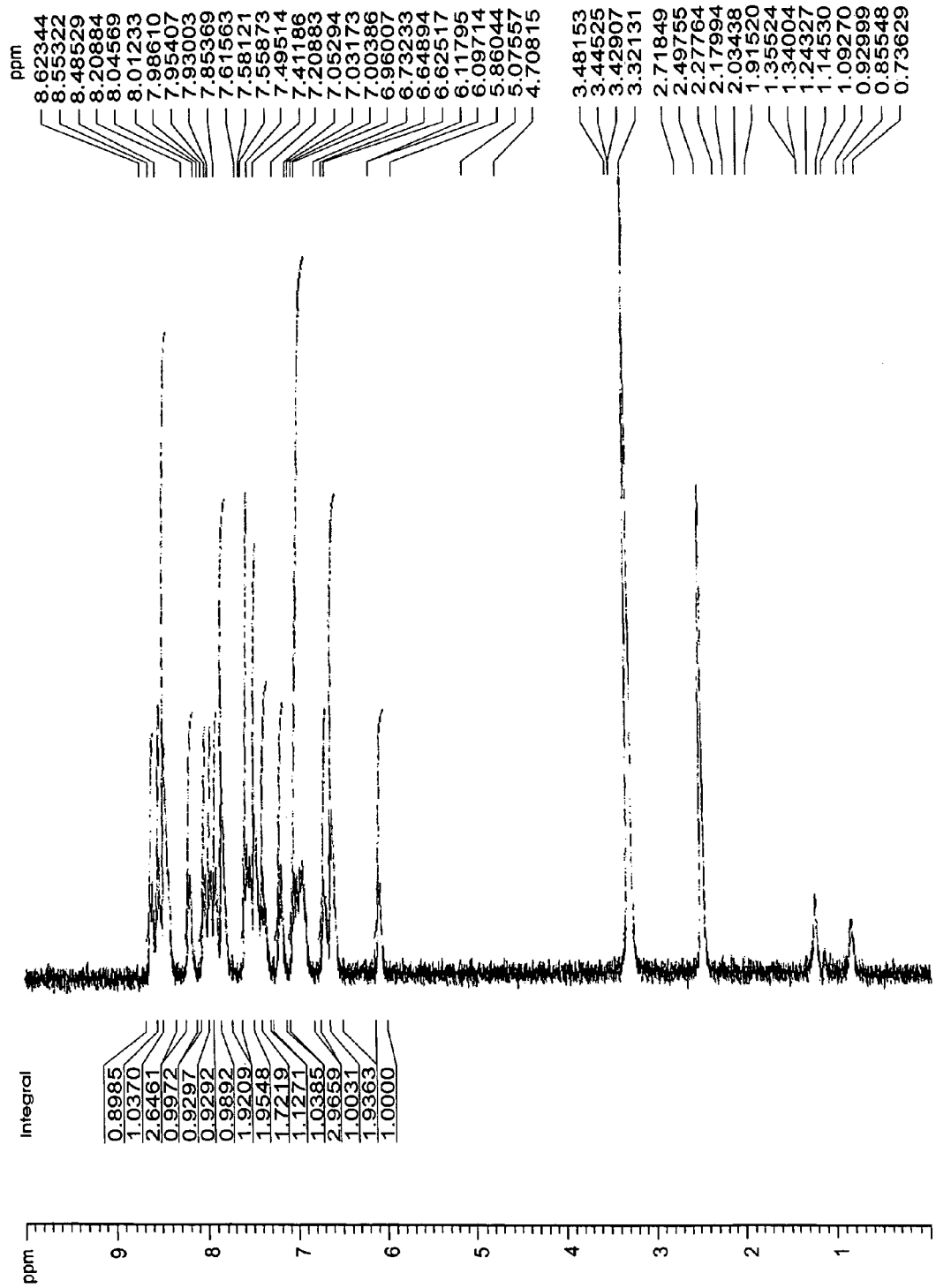
FIG. 5 shows the NMR spectrum of a compound of formula (5) according to the present invention.
Figure 6:
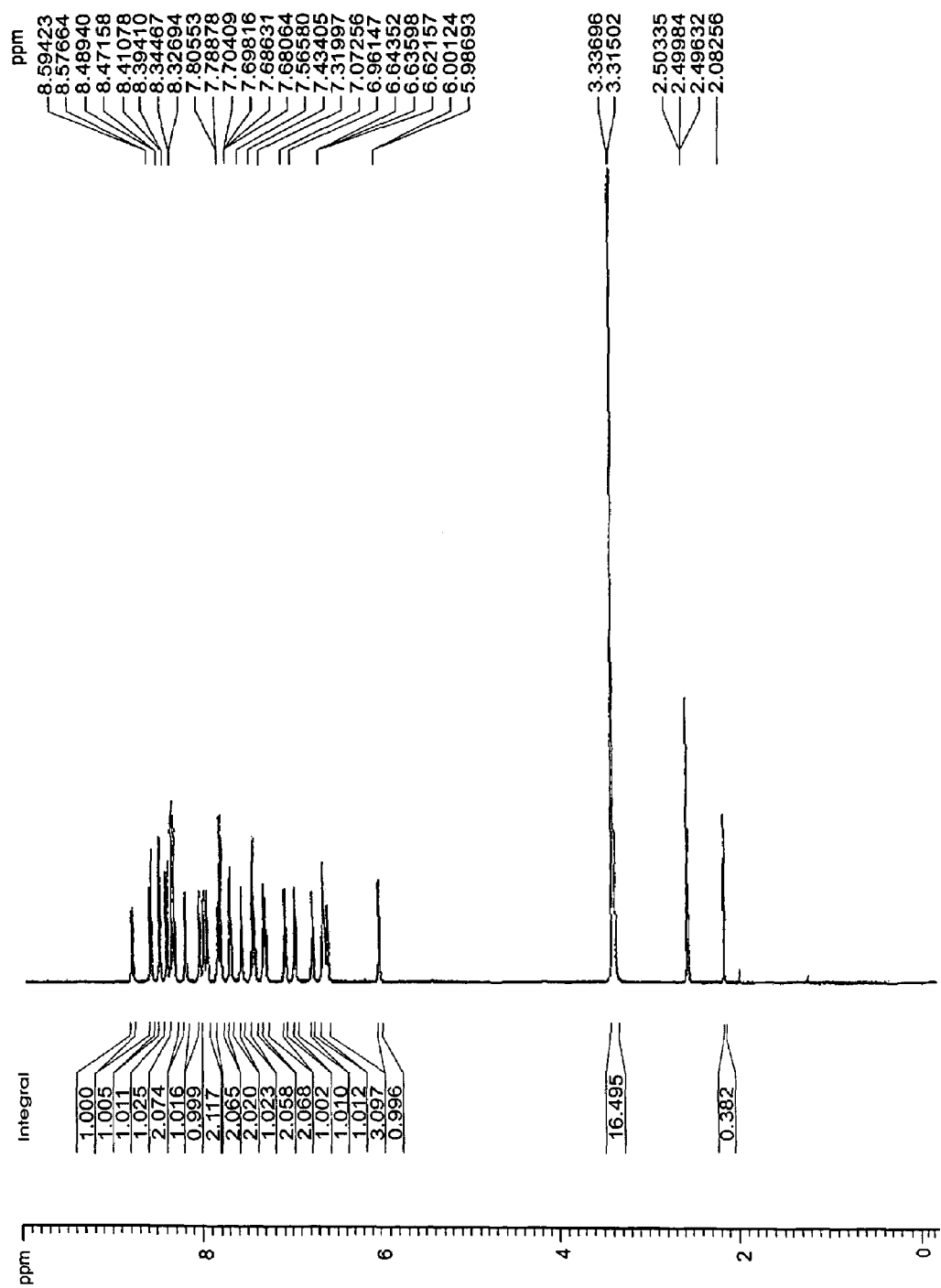
FIG. 6 shows the NMR spectrum of a compound of formula (6) according to the present invention.
Figure 7:
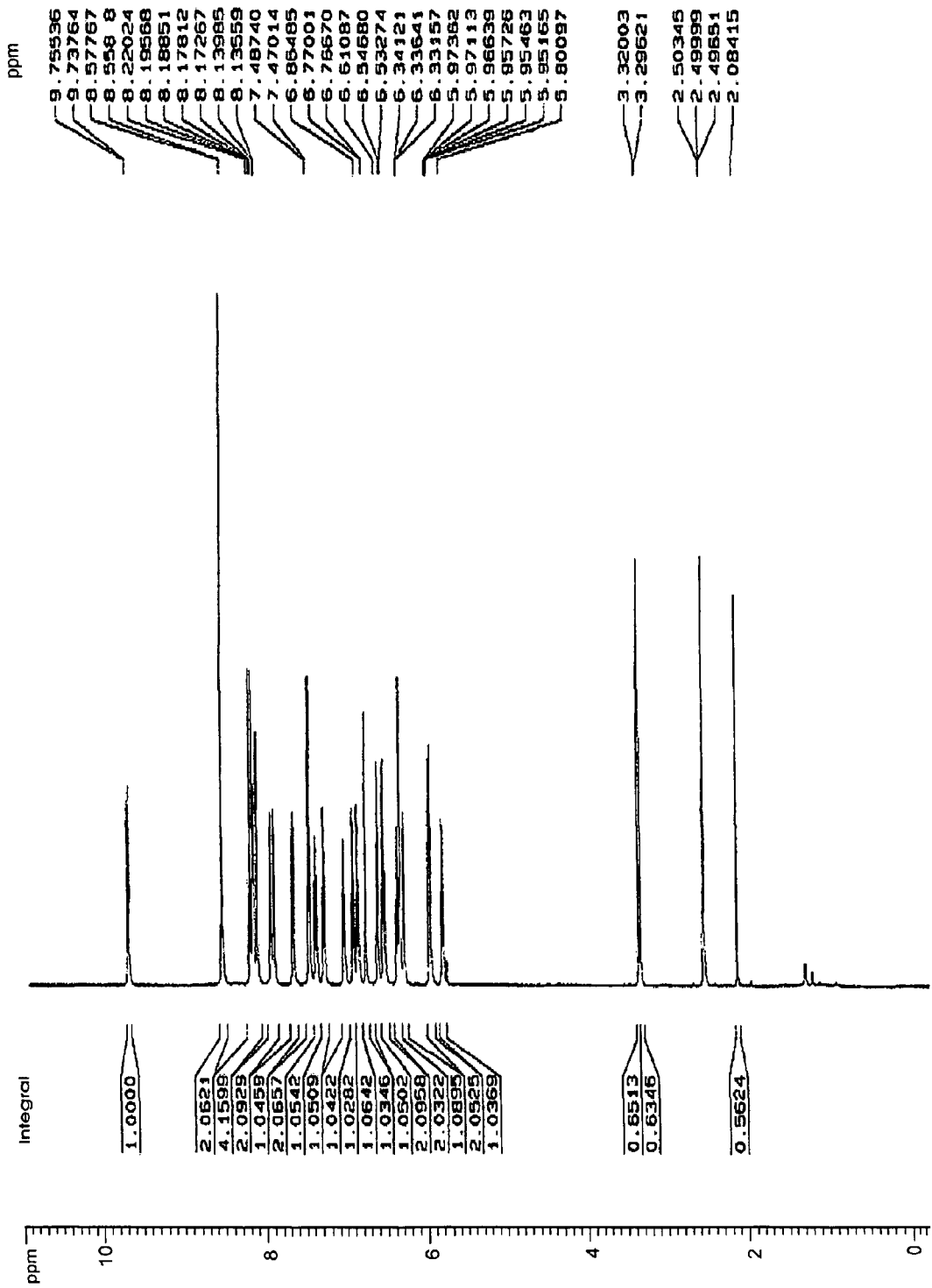
FIG. 7 shows the NMR spectrum of a compound of formula (7) according to the present invention.

Hereinafter, the present invention will be described in detail.

The present invention provides a compound of formula (1) below:

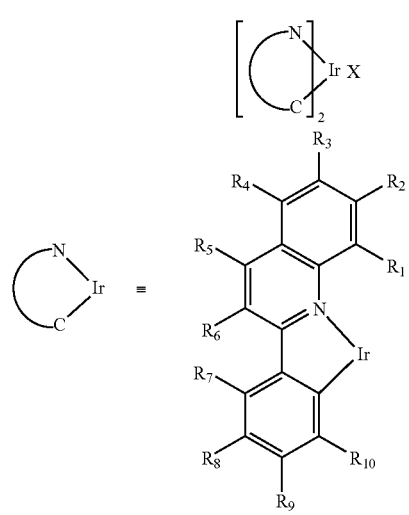

where $R_1$, $R_2$, $R_3$, $R_4$, $R_5$, $R_6$, $R_7$, $R_8$, $R_9$, and R10 are independently selected from the group consisting of hydrogen, a substituted or unsubstituted C1-C30 alkyl group, a substituted or unsubstituted C2-C20 alkenyl group, a substituted or unsubstituted C1-C20 alkoxy group, a substituted or unsubstituted C6-C30 aryl group, a substituted or unsubstituted C6-C30 fused aromatic ring, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C2-C20 heterocycloalkyl group, a halogen atom, and a cyano group, and X is a bidentate ligand.

A preferred example of the compound of formula (1) above has formula (1a) or formula (1b) below:

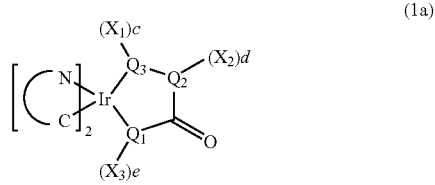

where $Q_1$, $Q_2$, and $Q_3$ are independently selected from the group consisting of carbon (C), oxygen (O), nitrogen (N), and sulfur (S); $X_1$, $X_2$, and $X_3$ are independently selected from the group consisting of hydrogen, a substituted or unsubstituted C1-C30 alkyl group, a substituted or unsubstituted C2-C20 alkenyl group, a substituted or unsubstituted C1-C20 alkoxy group, a substituted or unsubstituted C6-C30 aryl group, a substituted or unsubstituted C6-C30 fused aromatic ring, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C2-C20 heterocycloalkyl group, a halogen atom, and a cyano group; and c, d, and e are independently 0, 1, or 2, wherein $X_1$ and $X_2$ may be combined together to form a cyclic system.

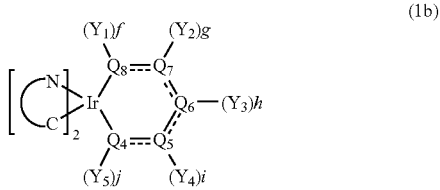

where $Q_4$, $Q_5$, $Q_6$, $Q_7$, $Q_8$, and $Q_9$ are independently selected from among carbon (C), oxygen (O), nitrogen (N), and sulfur (S); $Y_1$, $Y_2$, $Y_3$, $Y_4$, and $Y_5$ are independently a simple chemical bond or selected from the group consisting of hydrogen, a substituted or unsubstituted $C_1$-C30 alkyl group, a substituted or unsubstituted C2-C20 alkenyl group, a substituted or unsubstituted C1-C20 alkoxy group, a substituted or unsubstituted C6-C30 aryl group, a substituted or unsubstituted C6-C30 fused aromatic ring, a substituted or unsubstituted C6-C30 arylalkyl group, a substituted or unsubstituted C6-C30 aryloxy group, a substituted or unsubstituted C2-C30 heteroaryl group, a substituted or unsubstituted C2-C30 heteroarylalkyl group, a substituted or unsubstituted C2-C30 heteroaryloxy group, a substituted or unsubstituted C5-C20 cycloalkyl group, a substituted or unsubstituted C2-C20 heterocycloalkyl group, a halogen atom, and a cyano group; and f, g, h, I, and j are independently 0, 1, or 2, wherein two of the groups $Y_1$ through $Y_5$ may be combined together to form a cyclic system.

In formula (1a) above, $X_1$ and $X_2$ may be combined together to form a five- or six-membered ring, which may be fused.

In formula (1b) above, two of $Y_1$ through $Y_5$ may be fused. For example, $Y_1$ and $Y_2$, $Y_2$ and $Y_3$, $Y_3$ and $Y_4$, and/or $Y_4$ and $Y_5$ may be combined together to form a five- or six-membered ring, which may be fused.

In formula (1) above, $R_1$ through $R_{10}$ are independently selected from among hydrogen, methyl, ethyl, propyl, n-butyl, i-propyl, t-butyl, sec-butyl, t-amyl, neopentyl, trifluoromethyl, pentafluoroethyl, pentafluoroalkyl, heteroaryl, aryl, benzyl, 4-(tert-butyl)benzyl, 3,5-di-(tert-butyl)benzyl, 3,5-di(isopropyl)benzyl, naphthyl, phenyl, furyl, thienyl, pyridyl, a halogen atom, and cyano.

Examples of X in formula (1) above include acetylacetonate (acac), hexafluoroacetylacetonate, salicylidene (sal), picolinate (pic), 2-quinoline carboxylate, 8-hydroxyquinolinate, α-amino acid L-proline (L-pro), benzoylacetonate (bza), dibenzoylmethane (dbm), tetramethylheptanedione (tmd), and 1-(2-hydoxyphenyl)pyrazolate (oppz), which have formulae below where Ir as a ligand is illustrated for convenience.

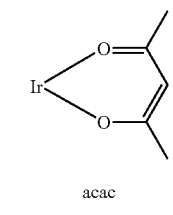

acac

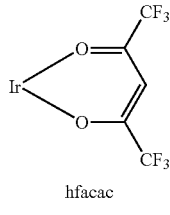

hfacac

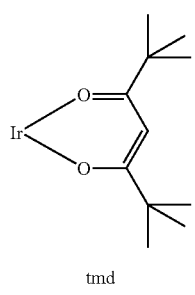

tmd

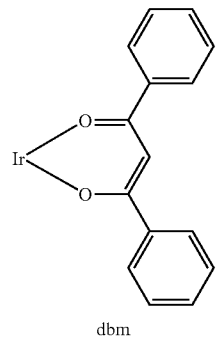

dbm

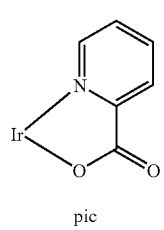

pic

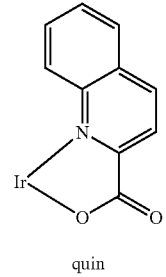

quin

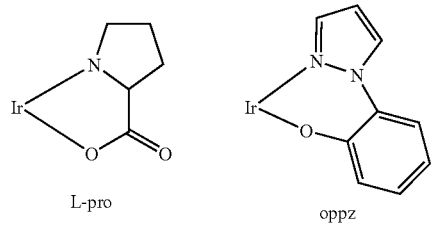

L-pro      oppz sal

Preferred examples of the red luminescent compound of formula (1) above include compounds having formulae (2) through (7) below.

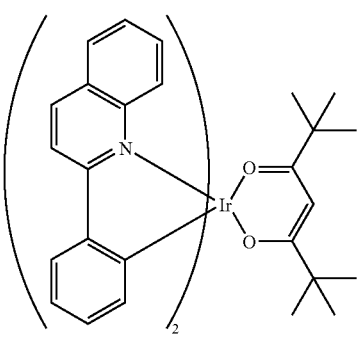

(2)

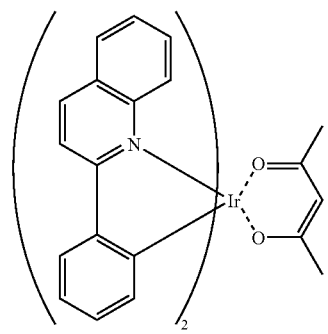

(3)

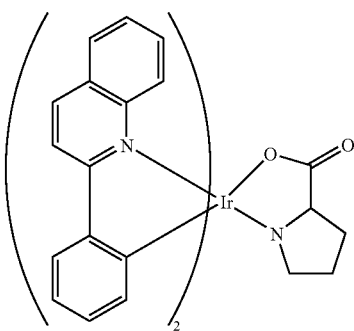

(4)

-continued

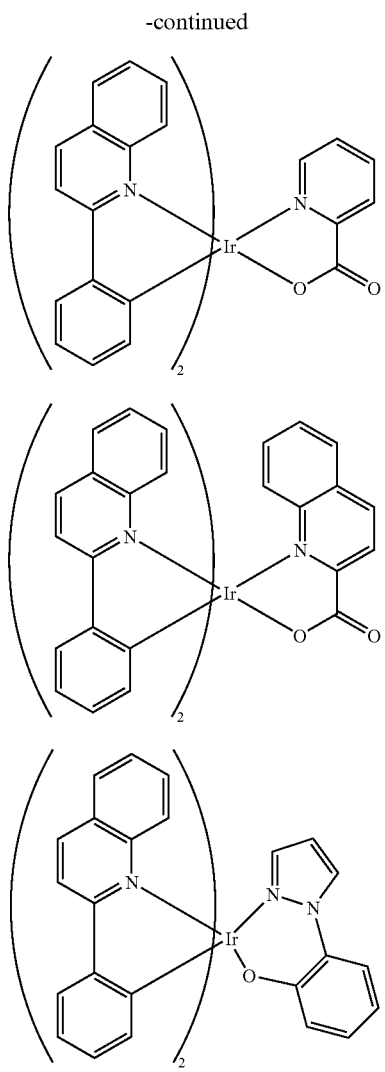

In formula (1) above, X may be a bidentate ligand expressed as:

A compound with such a bidentate ligand is expressed as formula (8) below:

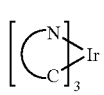

(8)

Examples of an unsubstituted C1-C30 alkyl group as a substitute group for a compound according to the present invention include methyl, ethyl, propyl, isobutyl, sec-butyl, pentyl, iso-amyl, hexyl, etc., wherein at least one hydrogen atom of the alkyl group may be substituted with a halogen atom, a C1-C30 alkyl group, a C1-C30 alkoxy group, a lower alkylamino group, a hydroxy group, a nitro group, a cyano group, an amino group, an amidino group, hydrazine, hydrazone, a carboxyl group, a sulfonic acid group, a phosphoric acid group, etc.

Examples of an unsubstituted C1-C20 alkoxy group as a substitute group for a compound according to the present invention include methoxy, ethoxy, propoxy, isobutyl, sec-butyloxy, pentyloxy, iso-amyloxy, hexyloxy, etc, wherein at least one hydrogen atom of the alkoxy group can be substituted with any substitute group described above as being suitable for the C1-C30 alkyl group.

The aryl group as a substitute group for a compound according to the present invention means a C6-C30 carbocyclic aromatic system containing at least one ring wherein such rings may be attached together in a pendent manner or may be fused. The term "aryl" embraces aromatic systems, such as phenyl, naphthyl, tetrahydronaphthyl etc. At least one hydrogen atom of the aryl group can be substituted with any substitute group described above as being suitable for the C1-C30 alkyl group.

The arylalkyl group as a substitute group for a compound according to the present invention means the above-defined aryl group having lower alkyl substitute groups, for example, methyl, ethyl, propyl, etc. for some hydrogen atoms. Examples of an arylalkyl group include benzyl, phenylethyl, etc. At least one hydrogen atom of the arylalkyl group can be substituted with any substitute group described above as being suitable for the C1-C30 alkyl group.

The heteroaryl group as a substitute group for a compound according to the present invention means a C2-C30 monocarbocyclic system containing one, two, or three hetero atoms selected from the group consisting of N, O, P, and S and having at least one ring wherein such rings may be attached together in a pendent manner or may be fused.

The heteroarylalkyl group as a substitute group for a compound according to the present invention means the above-defined heteroaryl group having lower alkyl substitute groups for some hydrogen atoms, wherein at least one hydrogen atom of the heteroarylalkyl group can be substituted with any substitute group described above as being suitable for the C1-C30 alkyl group.

The cycloalkyl group as a substitute group for a compound according to the present invention means a C4-C30 monovalent monocyclic system, wherein at least one hydrogen atom of the cycloalkyl group can be substituted with any substitute group described above as being suitable for the C1-C30 alkyl group.

The heterocycloalkyl group as a substitute group for a compound according to the present invention means a C1-C30 monovalent monocarbocyclic system containing one, two, or three hetero atoms selected from the group consisting of N, O, P, and S and having lower alkyl substitute groups for some hydrogen atoms, wherein at least one hydrogen atom of the heterocycloalkyl group can be substituted with any substitute group described above as being suitable for the C1-C30 alkyl group.

The fused aromatic ring as a substitute group for a compound according to the present invention means cyclic compounds containing at least two rings fused by sharing two atoms, wherein at least one hydrogen atom of the ring can be substituted with any substitute group described above as being suitable for the C1-C30 alkyl group.

The compound of formula (1) according to the present invention is a red luminescent material and offers higher energy transfer efficiency and luminescent efficiency due to its specific conformation. The compound according to the present invention is applicable to various image display devices, and especially as a host material or dopant used to form an emissive layer of organic EL devices.

A synthesis method of the compound of formula (1) below will be described.

A compound of formula (1) is manufactured via reaction between a compound of formula (9) below and a compound (XH) with a ligand X. Examples of X in the compound XH are the same as described above. The compound XH is used in an amount of 2-3 moles with reference to 1 mole of the compound of formula (9). Reaction temperature varies, depending on the kind of solvent, in a range of 70-100° C.

Any solvent can be used for the reaction without limitation, with ethanol being preferred. When ethanol is used as the solvent, ethanol is used in an amount of 1,500-2,000 parts by weight with reference to 100 parts by weight of the compound of formula (9). A base is used for the reaction. Suitable examples of a base include $K_2CO_3$, $Ca_2CO_3$, etc.

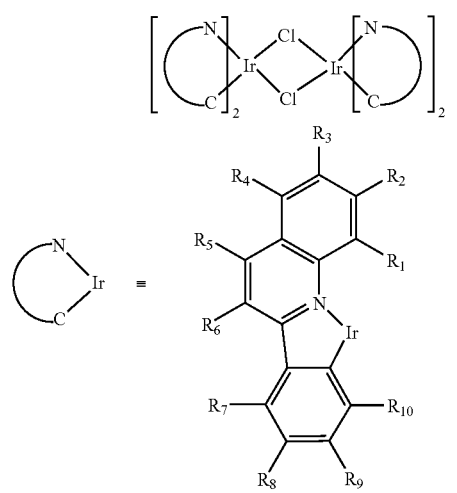

(9)

In the formula (9) above, $R_1$, $R_2$, $R_3$, $R_4$, $R_5$, $R_6$, $R_7$, $R_8$, $R_9$, and $R_{10}$ are the same as described in the formula (1).

The compound of formula (9) above is synthesized by the reaction of a ω-phenylquinoline compound of formula (10) with iridium chloride ($IrCl_3$). ⅙-½ moles of iridium chloride is reacted with 1 mole of ω-phenylquinoline compound. Reaction temperature is in a range of 70-100° C.

Suitable solvents for the reaction include 2-ethoxyethanol, water, glycerol, etc. The amount of the solvent is in a range of 2,000-3,000 parts by weight with respect to 100 parts by weight of the compound of formula (10) below.

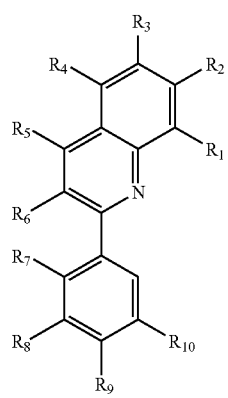

(10)

Hereinafter, an organic EL device using the compound of formula (1) and a method of manufacturing the organic EL device will be described in detail.

The compound of formula (1) is available as a material for forming an emissive layer of an organic EL device. A method of manufacturing an organic EL device, as illustrated in FIG. 1, according to an embodiment of the present invention using the compound of formula (1) is described below.

Referring to FIG. 1, a first electrode 12 is initially formed as a pattern on a surface of a substrate 11. A substrate commonly used in organic EL devices is used for the first electrode 12. A preferred substrate is a glass substrate or a transparent plastic substrate that is transparent, easy to handle, and waterproof and has an even surface. It is preferable that the substrate 11 has a thickness of 0.3-0.7 mm.

The first electrode 12 is made of a conductive metal which allows for an easy hole injection or a conductive metal oxide. Examples of a material for the first electrode 12 include indium tin oxide (ITO), indium zinc oxide (IZO), nickel (Ni), platinum (Pt), gold (Au), iridium (Ir), etc.

The substrate 11 with the first electrode 12 is washed, for example, using organic solvent, such as isopropanol (IPA), acetone, etc. After the washing, the substrate 11 is subjected to UV/ozone treatment.

Next, a hole injecting layer (HIL) 13 is optionally formed on the first electrode 12 of the substrate 11. The HIL 13 reduces contact resistance between the first electrode 12 and a hole transporting layer (HTL) 14 and improves the ability of the HTL 14 to transport holes from the first electrode 12 to an emissive layer (EML) 15 and the driving voltage and lifespan properties of the device. Suitable materials for the HIL 13 include water-soluble PEDOT (poly(3,4-ethylenedioxythiophene)), PSS(polystyrene parasulfonate), starburst amines, such as IDE 406 (available from Idemitsu Kosan Co.), etc. The first electrode 12 is coated with such a material and dried to form the HIL 13.

When water-soluble PEDOT is used for the HIL 13, it is preferable to dry the coated layer at a temperature of 100-250° C., more preferably, at about 200° C. For materials compatible with vacuum deposition for forming HIL 13, no additional process such as the drying process is required after the formation of the HIL 13 prior to deposition of a next layer.

Next, the HTL 14 is formed on the HIL 13.

Materials for the HTL 14 are not specifically limited. For example, the materials for the HTL 14 include, but not limited to, N,N'-bis(3-methylphenyl)-N,N'-diphenyl-[1,1-biphenyl]-4,4'-diamine(TPD), N,N'-di(naphthalene-1-yl)-N,N'-diphenyl benzidine{N,N'-di(naphthalene-1-yl)-N,N'-diphenyl-benzidine(NPB)} of formula (11) below, etc. The HTL 14 may be formed by any method, such as spin coating, vacuum deposition. Vacuum deposition is preferred for lower molecular weight materials.

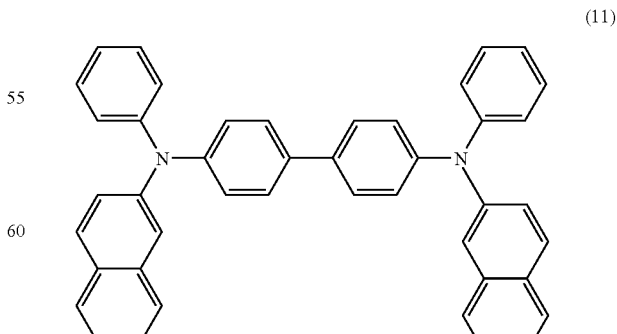

(11)

Next, the EML 15 is formed on the HTL 14. The EML 15 may be made of a compound of formula (1) above alone or in combination with a conventional host material. In the latter case, the compound of formula (1) acts as a dopant. A suitable host material includes 4,4'-bis(carbazol-9-yl)-biphenyl (CBP) of the formula (12), etc.

(12)

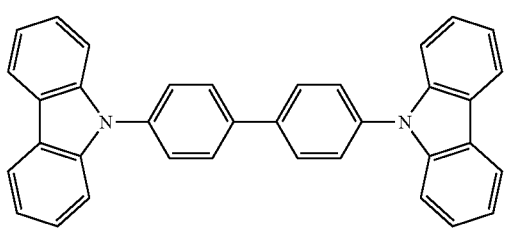

Any method, for example, simultaneous deposition, can be applied to form the EML layer 15. The amount of the compound of formula (1) as a dopant is not limited. However, it is preferable that the amount of the compound of formula (1) above as a dopant is in a range of 5-40 parts by weight with respect to 100 parts by weight of the material for forming the EML layer 15. If the amount of the dopant is not within the above range, the EL device offers poor luminescent properties.

It is preferable that the EML layer 15 has a thickness of 100-500 Å. If the thickness of the EML layer 15 is smaller than 100 Å, luminescent efficiency becomes low. If the thickness of the EML layer 15 is greater than 500 Å, the driving voltage becomes high.

A hole barrier layer (HBL) 16 is formed on the EML layer 15. The HBL 16 prevents excitons, which are generated from emissive material in the EML layer 15, or holes from migrating into an electron transporting layer (ETL) 17. Suitable materials for the HBL 16 include phenanthrolines, such as BCP available from Universal Display Corporation (UDC); triazoles; oxadiazoles, such as PBD; aluminum complexes (available from UDC), such as BAlq having a formula below, etc. Any method can be applied to form the HBL 16 without limitations. For example, vacuum deposition or spin coating may be applied to form the HBL 16, depending on the material for the HBL 16.

The ETL 17 is formed on the HBL 16. Suitable materials for the ETL 17 include a compound of formula (13) below; oxazoles; isooxazoles; triazoles; isothiazoles; oxadiazoles; thiadiazoles; perylenes of a formula below; aluminum complexes, such as Alq3 (tris(8-quinolinolato)-aluminum), BAlq, SAlq, and Almq3, which have a formula below; gallium complexes, such as Gaq'$_2$OPiv, Gaq'$_2$OAc, and 2(Gaq'$_2$), which have a formula below, etc. Vacuum deposition or spin coating may be applied to form the ETL 17, depending on the material for the ETL 17.

(13)

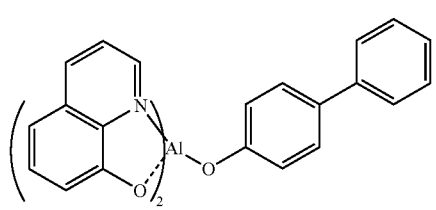

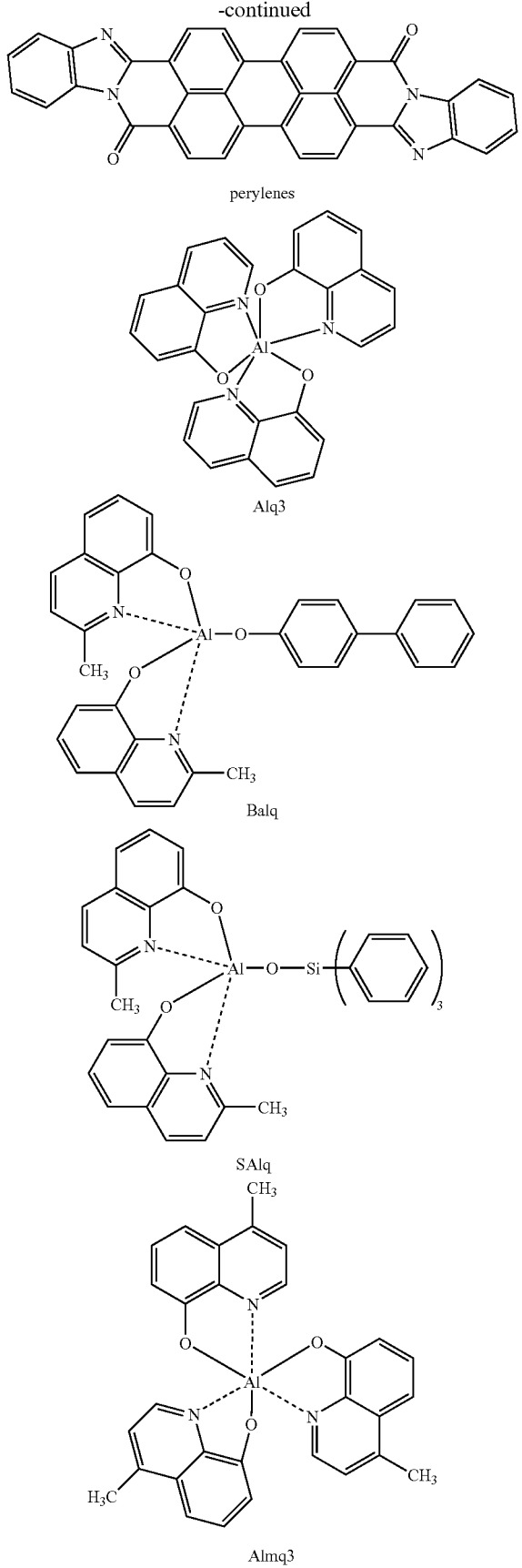

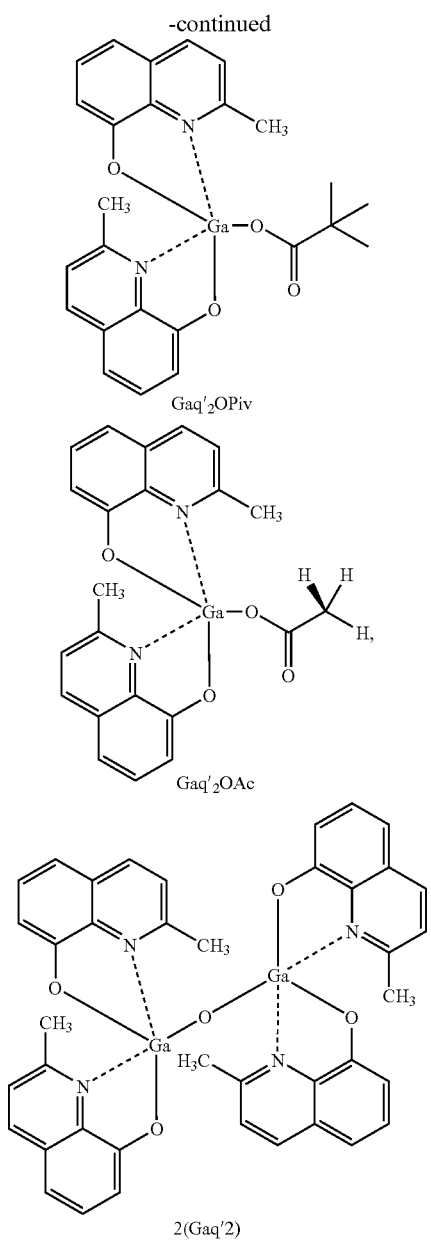

Gaq'₂OPiv

Gaq'₂OAc

2(Gaq'2)

Next, an electron injecting layer (EIL) 18 is formed on the ETL 17. Materials for the EIL 18 include Alq3 having a formula above, LiF, NaCl, CsF, etc. Vacuum deposition or spin coating may be applied to form the EIL 18. It is preferable that the EIL 18 has a thickness of 1-15 Å.

Next, a second electrode 19 is formed on the EIL 18, followed by sealing to complete the manufacture of an organic EL device.

The second electrode 19 is made of a low work function metal, for example, Li, Ca, LiF/Ca, LiF/Al, Al, Mg, or a Mg alloy, by deposition. It is preferable that the second electrode 19 has a thickness of 800-3000 Å.

An organic EL device according to the present invention may have a stacked structure as illustrated in FIG. 1 or further with an additional single or dual intermediate layer if required. The HIL 13, the HBL 16, and the EIL 18 are optional.

The present invention will be described in greater detail with reference to the following examples. The following examples are illustrative purposes and are not intended to limit the scope of the invention.

The structure of the compounds synthesized in the following examples was identified using $^1$H-NMR, $^{13}$C-NMR, UV, and a spectrofluorometer. $^1$H-NMR and $^{13}$C-NMR were measured using a Bruker AM-300 spectrometer. UV characteristics were measured using a BECKMAN) DU-650. The spectrofluorometer used was JASCO FP-750.

Reaction scheme 1 is for Synthesis Examples 1 and 2.

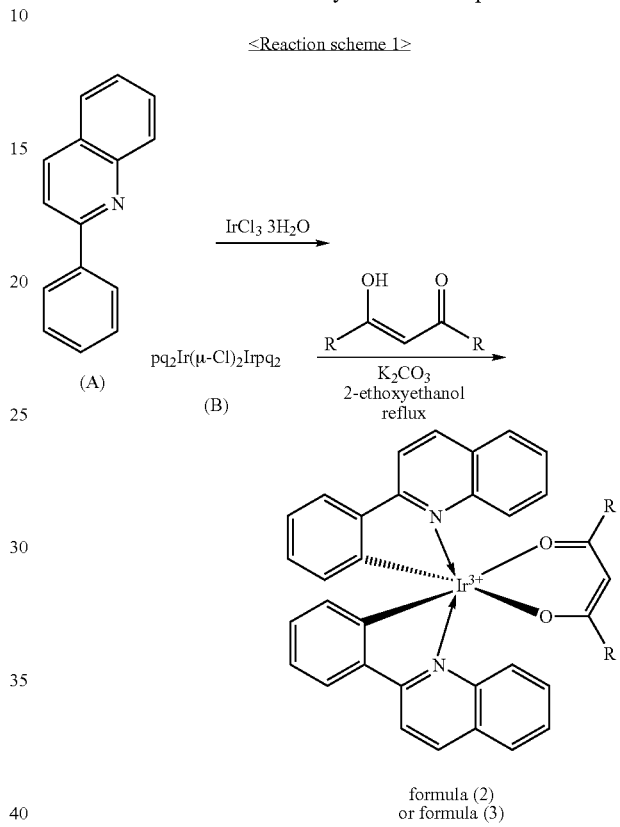

<Reaction scheme 1> formula (2) or formula (3)

SYNTHESIS EXAMPLE 1

Compound of Formula (2)

1 mmol of iridium chloride (IrCl₃.3H₂O) and 6 mmol of ω-phenylquinoline (A) were added into a mixed solution of 22.5 mL of 2-ethoxyethanol and 7.5 mL of water and refluxed for 48 hours to provide compound (B).

1 mmol of the compound (B), 2.5 mmol of 2,2,6,6-tetramethylheptane-3,5-dione (tmd), and 10 mL of 2N—K₂CO₃ solution were added into 20 mL of ethanol and refluxed for 48 hours, followed by filtration of a resulting solid. The filtered solid was washed using ethanol and then acetone to provide a compound of formula (2) above with a yield of 85%.

$^1$H-NMR(CDCl₃, 500 MHz): (ppm) 8.48 (d, 2H), 8.38(d, 2H), 8.26(d, 2H), 7.99(t, 4H), 7.53 (t, 21H), 7.39 (t, 21H), 6.89 (t,4H), 6.55(t, 2H), 6.37(d, 2H), 4.90(s, 1H), 0.56 (s, 6H)

SYNTHESIS EXAMPLE 2

Compound of Formula (3)

1 mmol of iridium chloride (IrCl₃.3H₂O) and 6 mmol of ω-phenylquinoline (A) were added into a mixed solution of 22.5 mL of 2-ethoxyethanol and 7.5 mL of water and refluxed for 48 hours to provide compound (B).

1 mmol of the compound (B), 2.5 mmol of acetylacetone (acacH), and 10 mL of 2N—K$_2$CO$_3$ solution were added into 20 mL of ethanol and refluxed for 48 hours to obtain a white solid. The white solid was filtered and washed using ethanol and then acetone to provide a compound of formula (3) above with a yield of 85%.

$^1$H-NMR(CDCl$_3$, 500 MHz): (ppm) 8.50 (d, 2H), 8.38 (d, 2H), 8.26 (d, 2H), 8.02 (d, 2H), 7.99 (d,2H), 7.55 (m, 21H), 6.87 (t,4H), 6.54 (t, 2H), 6.289(d, 2H), 4.70 (s, 1H), 1.46 (s, 6H)

SYNTHESIS EXAMPLE 3

Compound of Formula (4)

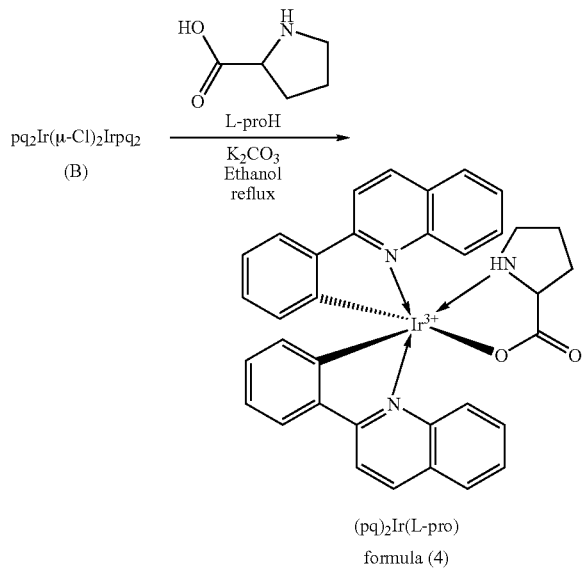

(pq)$_2$Ir(L-pro)

formula (4)

1 mmol of iridium chloride (IrCl$_3$.3H$_2$O) and 6 mmol of ω-phenylquinoline (A) were added into a mixed solution of 22.5 mL of 2-ethoxyethanol and 7.5 mL of water and refluxed for 48 hours to provide compound (B).

1 mmol of the compound (B), 2.5 mmol of α-amino acid L-proline (L-proH), and 10 mL of 2N—K$_2$CO$_3$ solution were added into 20 mL of ethanol and refluxed for 48 hours, followed by filtration of a resulting solid. The filtered solid was washed with ethanol and then acetone to provide a red compound of formula (4) above with a yield of 85%.

$^1$H-NMR(CDCl$_3$, 300 MHz): (ppm) 8.70 (m, 1H),8.49 (m, 3H), 8.35 (d, 12H), 8.09 (m, 3H), 7.64 (m, 3H), 7.57 (m, 1H), 7.39 (t, 1H), 6.95 (m,1H), 6.86 (m, 1H), 6.77 (m, 1H),6.66 (m, 1H),6.49 (m, 1H) 5.93 (d, 1H), 5.56 (m, 1H),2.50 (m, 1H),1.21 (m,5H)

SYNTHESIS EXAMPLE 4

Compound of Formula (5)

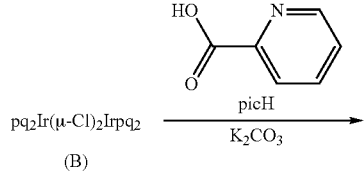

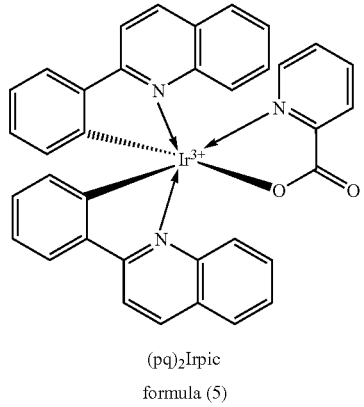

(pq)$_2$Irpic formula (5)

1 mmol of iridium chloride (IrCl$_3$.3H$_2$O) and 6 mmol of ω-phenylquinoline (A) were added into a mixed solution of 22.5 mL of 2-ethoxyethanol and 7.5 mL of water and refluxed for 48 hours to provide compound (B).

1 mmol of the compound (B), 2.5 mmol of picolinate (picH), and 10 mL of 2N—K$_2$CO$_3$ solution were added into 20 mL of ethanol and refluxed for 48 hours, followed by filtration of a resulting solid. The filtered solid was washed with ethanol and then acetone to provide a red compound of formula (5) above with a yield of 80%.

$^1$H-NMR(CDCl$_3$, 500 MHz): 8.64 (d, 1H, J 8.6 Hz), 8.57 (d, 1H, J 8.7 Hz), 8.48 (m, 3H), 8.22 (d, 1H, J 7.9 Hz), 8.06 (d, 1H, J 7.5 Hz), 8.00 (d, 1H, J 7.2 Hz), 7.94 (d, 1H, J 9.3 Hz), 7.85 (m, 2H), 7.60 (d, 1H, J 7.3 Hz), 7.56 (m, 1H), 7.50 (m, 2H), 7.41 (m, 1H), 7.22 (d, 1H, J 8.7 Hz), 7.05 (t, 1H, J 15.8 Hz), 6.96 (m, 2H), 6.73 (t, 1H, J 14.1 Hz), 6.64 (m, 2H), 6.11 (d, 1H, J 7.3 Hz).

SYNTHESIS EXAMPLE 5

Compound of Formula (6)

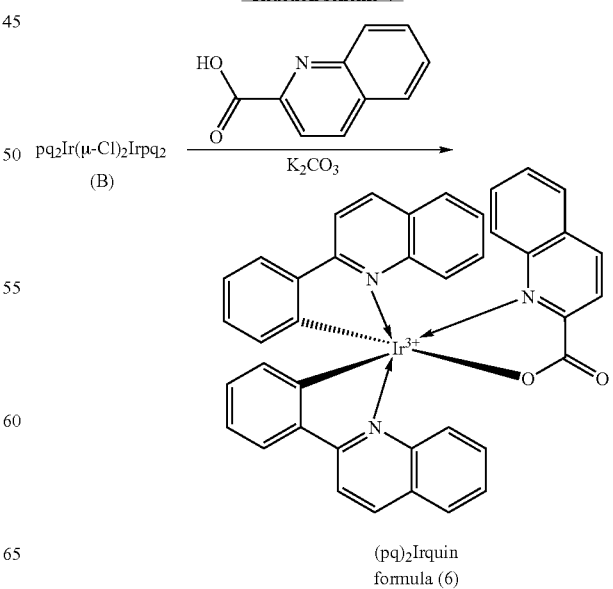

(pq)$_2$Irquin formula (6)

1 mmol of iridium chloride (IrCl₃.3H₂O) and 6 mmol of ω-phenylquinoline (A) were added into a mixed solution of 22.5 mL of 2-ethoxyethanol and 7.5 mL of water and refluxed for 48 hours to provide compound (B).

1 mmol of the compound (B), 2.5 mmol of 2-quinoline carxylate, and 10 mL of 2N—K₂CO₃ solution were added into 20 mL of ethanol and refluxed for 48 hours, followed by filtration of a resulting solid. The filtered solid was washed with ethanol and then acetone to provide a red compound of formula (6) above with a yield of 80%.

¹H-NMR(CDCl₃, 300 MHz): 8.80 (d, 1H, J 9.7 Hz), 8.59 (d, 1H, J 8.8 Hz), 8.48 (d, 1H, J 8.8 Hz), 8.40 (d, 1H, J 8.5 Hz), 8.33 (m, 2H), 8.20 (d, 1H, J 7.8 Hz), 8.01 (m, 3H), 7.83 (m, 2H), 7.70 (d, 2H, J 8.9 Hz), 7.57 (d, 1H, J 15.8 Hz), 7.44 (m, 2H), 7.32 (m, 2H), 7.06 (t, 1H, J 25.7 Hz), 6.96 (t, 1H, J 15.0 Hz), 6.76 (t, 1H, 14.5 Hz), 6.65 (m, 3H), 6.00 (d, 1H, J 7.7 Hz).

SYNTHESIS EXAMPLE 6

Compound of Formula (7)

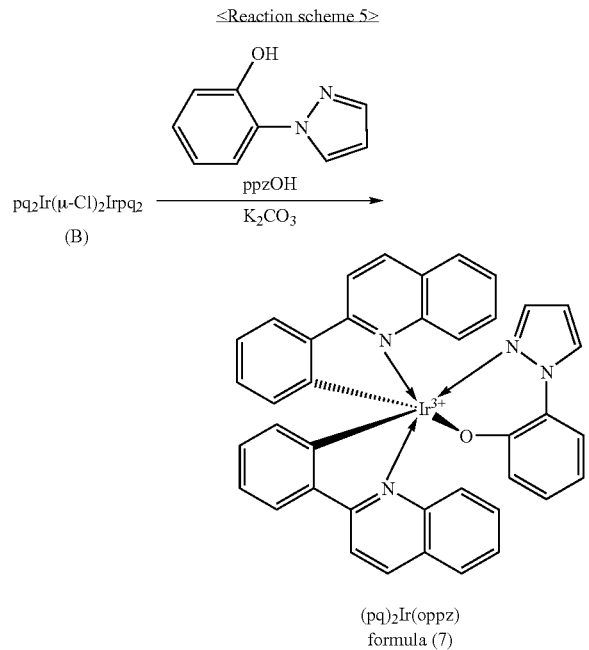

(pq)₂Ir(oppz)
formula (7)

1 mmol of iridium chloride (IrCl₃.3H₂O) and 6 mmol of ω-phenylquinoline (A) were added into a mixed solution of 22.5 mL of 2-ethoxyethanol and 7.5 mL of water and refluxed for 48 hours to provide compound (B).

1 mmol of the compound (B), 2.5 mmol of α-amino acid 1-(2-hydroxyphenyl)pyrazolate (ppzoH), and 10 mL of 2N—K₂CO₃ solution were added into 20 mL of ethanol and refluxed for 48 hours, followed by filtration of a resulting solid. The filtered solid was washed with ethanol and then acetone to provide a red compound of formula (7) above with a yield of 80%.

Each of the compounds of formulae (2) through (4) obtained in Synthesis Examples 1 through 3 was dissolved in methylene chloride and used for a photoluminescence (PL) spectrum measurement. The resulting spectra of the compounds are shown in FIG. 8.

Figure 8:
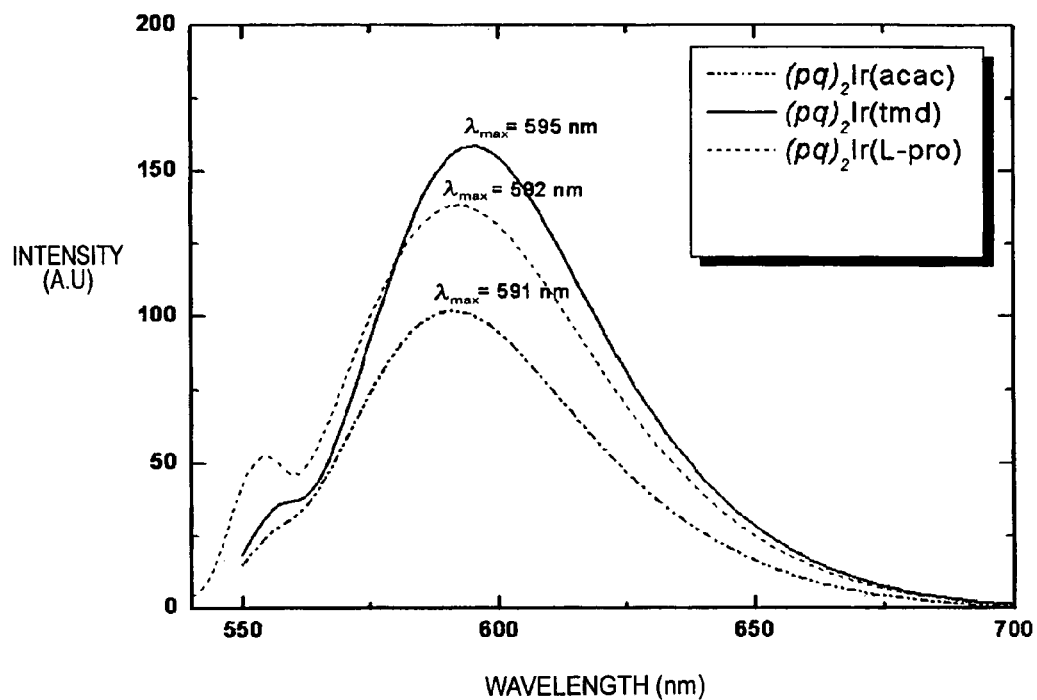
FIG. 8 shows the photoluminescence (PL) spectra of the compounds of formulae (2) through (4)

As is apparent from FIG. 8, the PL intensities of the compound of formula (2) and the compound of formula (4) are about 170% and about 140%, respectively, greater than the compound of formula (3). In addition, a peak luminance of the compound of formula (2), which occurs at 595 nm, is highest among the three compounds, indicating that the compound of formula (2) is brightest red.

EXAMPLE 1

An indium tin oxide (ITO) substrate (available from Coring Co.) having a resistance of 10 Ω/cm² was used for an anode. A hole injecting layer was formed of IDE 406 on the anode to a thickness of 600 Å by vacuum deposition. Next, a hole transporting layer was formed on the hole injecting layer by depositing the compound of formula (5) above in a vacuum to a thickness of 300 Å. An emissive layer was formed on the hole transporting layer by spin coating a mixture of 12 parts by weight of the compound of formula (2) above and 88 parts by weight of CBP of formula (6) above to a thickness of 300 Å.

A hole barrier layer was formed on the emissive layer by depositing the compound of formula (7) above in a vacuum to a thickness of 50 Å. An electron transporting layer was formed on the HBL layer by depositing Alq3 in a vacuum to a thickness of 200 Å. Finally, a LiF/Al electrode was formed on the electron transporting layer by sequentially depositing LiF to a thickness of 10 Å and Al to a thickness of 3,000 Å in a vacuum, thereby resulting in a complete organic EL device.

EXAMPLES 2 AND 3

Organic EL devices were manufactured in the same manner as in Example 1 except that the compound of formula (3) and the compound of formula (4), instead of the compound of formula (2), were used, respectively, to form the emissive layer.

The luminance, the chromaticity coordinate, and the efficiency of the organic EL device manufactured in Example 1 were measured. The results are shown in Table 1 below.

TABLE 1

| Voltage (V) | Current density (mA/cm²) | Luminance | Current efficiency (Cd/A) | Power efficiency (lm/W) | CIE(x, y) |
|---|---|---|---|---|---|
| 3 | 0.1262 | 8.897 | 7.0480 | 7.3807 | (0.62, 0.37) |
| 3.5 | 1.0172 | 82.51 | 8.1114 | 7.2808 | (0.62, 0.37) |
| 4 | 3.1626 | 258.4 | 8.1704 | 6.4170 | (0.62, 0.37) |
| 4.5 | 6.9463 | 551.8 | 7.9439 | 5.5459 | (0.62, 0.37) |
| 5 | 13.1024 | 992.9 | 7.5780 | 4.7614 | (0.62, 0.37) |
| 5.5 | 22.4044 | 1603 | 7.1549 | 4.0868 | (0.62, 0.37) |
| 6 | 35.6763 | 2394 | 6.7103 | 3.51353 | (0.62, 0.37) |
| 6.5 | 53.7675 | 3374 | 6.2752 | 2.0319 | (0.62, 0.37) |
| 7 | 77.865 | 4583 | 5.8858 | 2.6415 | (0.62, 0.37) |

As is apparent from Table 1, the organic EL device manufactured in Example 1 has high current and power efficiency, is operable at low voltages, and has appropriate chromaticity coordinates as a red luminescent material.

Figure 9:
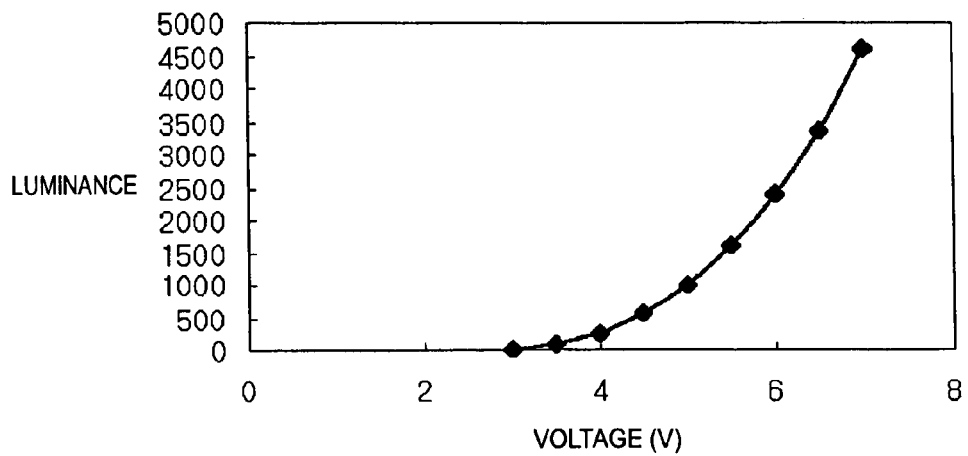
FIG. 9 is a graph of luminance versus voltage for an organic EL device manufactured in Example 1 according to the present invention.
Figure 10:
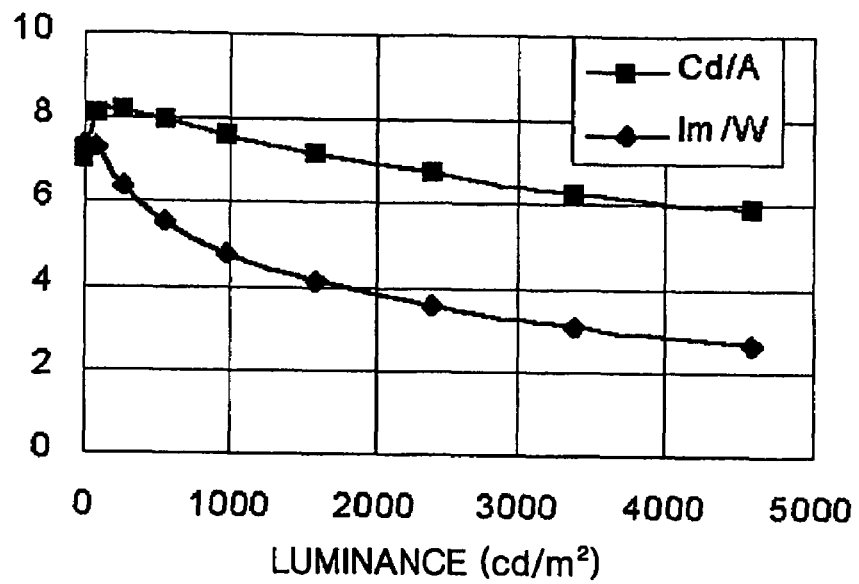
FIG. 10 is a graph of current efficiency (Cd/A) and power efficiency (lm/W) for the organic EL device manufactured in Example 1 according to the present invention.

The luminance-voltage characteristics and the luminescent efficiency of the organic EL device of Example 1 were measured. The results are shown in FIGS. 9 and 10. Referring to FIGS. 9 and 10, the organic EL device of Example 1 shows higher efficiency compared to when using fluorescent materials, which are believed to have a current efficiency of 3-5 cd/A.

The EL spectrum and the chromaticity coordinate characteristics of the organic EL device of Example 1 were measured. The results are shown in FIGS. 11 and 12.

Figure 11:
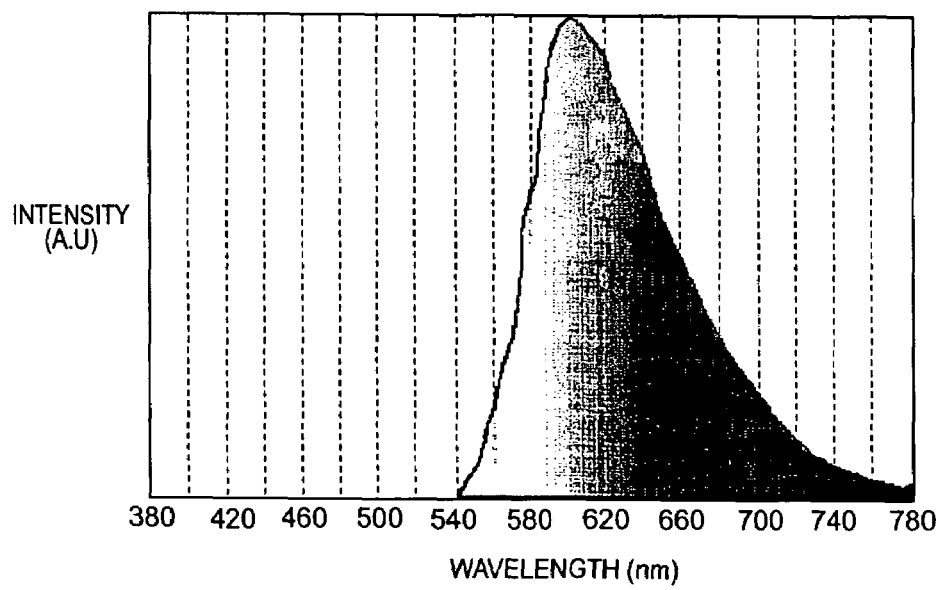
FIG. 11 shows the EL spectrum of the organic EL device manufactured in Example 1 according to the present invention.
Figures 12, 13:
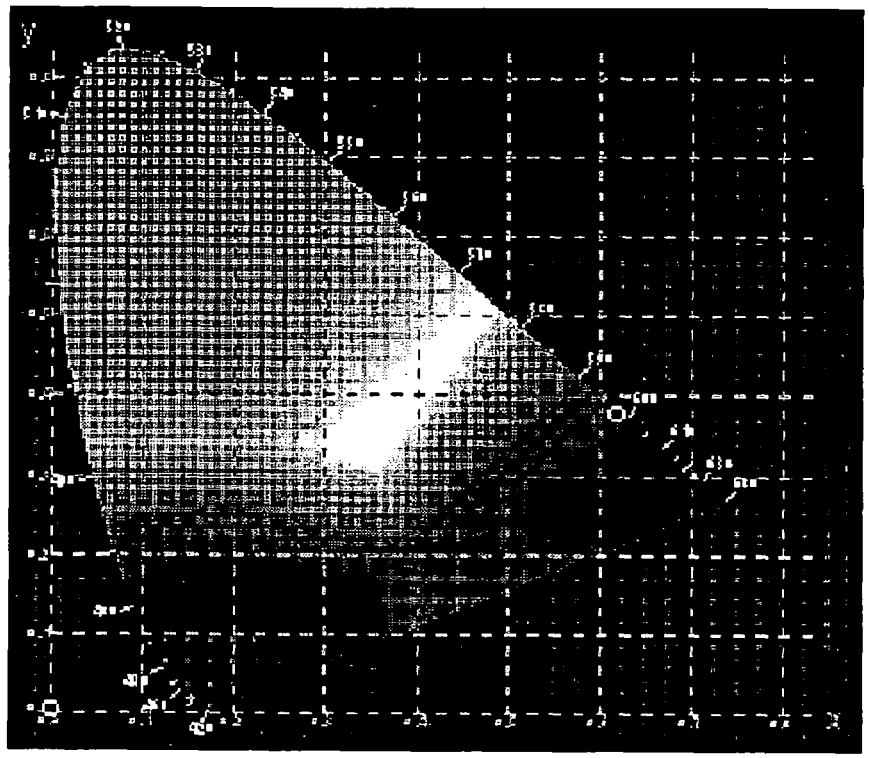
FIG. 12 is a chromaticity diagram for the organic EL device manufactured in Example 1 according to the present invention.
FIG. 13 is a table of maximum photoluminescent luminance and photoluminescent quantum yield for compounds of formulae (2) through (7).

Referring to FIGS. 11 and 12, the chromaticity coordinate of the organic EL device of Example 1 is close to brighter red wavelengths compared to when using fluorescent materials. The organic EL device of Example 1 shows a peak intensity near 600 nm, as shown in FIG. 11, indicating that the purity of the color red displayed is improved.

The maximum photoluminescent luminance and photoluminescent quantum yields of the compounds having formulas (2) through (7) above are in FIG. 13.

Referring to FIG. 13, the maximum phosphorescent luminance of the compounds of formulae (2) through (6) ranges from about 570 nm to about 600 nm. The photoluminescent quantum yields were measured in liquid state at 600 nm. As is apparent from FIG. 13, the red phosphorescent compounds according to the present invention are believed to be capable of emitting light of a red wavelength close to the NTSC standard when used in organic EL devices.

As described above, the red luminescent compounds according to the present invention have greater luminescent efficiency than conventional red fluorescent dopants, which are reported to have an efficiency of 3-5 cd/A (C. H. Chen, C. W. Tang et al. *Macromol. Symp.* (1997) 125, 49-58), and lower a driving voltage to 5-6V so that the amount of power consumed is greatly reduced. The red luminescent compounds according to the present invention can produce radiation having a desired chromaticity and have superior color display properties than fluorescent materials.

A compound of formula (1) above according to the present invention is a red luminescent compound applicable to various image display devices. When used for the emissive layer of an organic EL device, the compound of formula (1) provides improved luminescent efficiency and driving voltage characteristics and reduces power consumption in the organic EL device, compared to conventional red luminescent materials.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A compound having the formula (1):

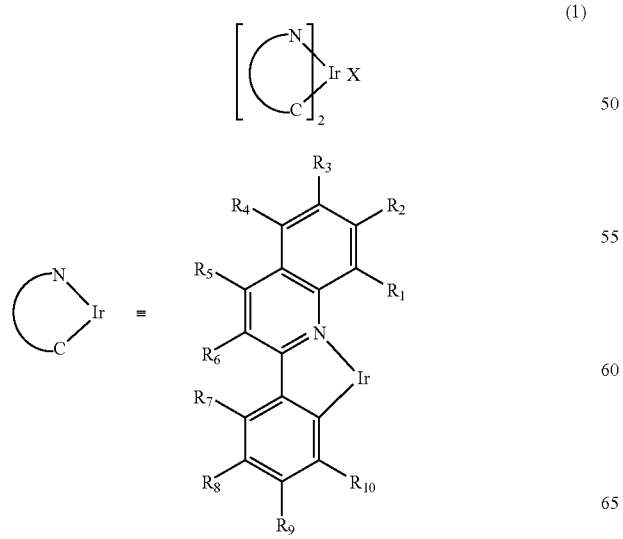

where $R_1$, $R_2$, $R_3$, $R_4$, $R_5$, $R_6$, $R_7$, $R_8$, $R_9$, and $R_{10}$ are hydrogen, and X is a bidentate ligand selected from the group consisting of α-amino acid L-proline, 2-quinoline carboxylate, and 1-(2-hydoxyphenyl) pyrazolate.

2. The compound of claim 1, having the formula (4):

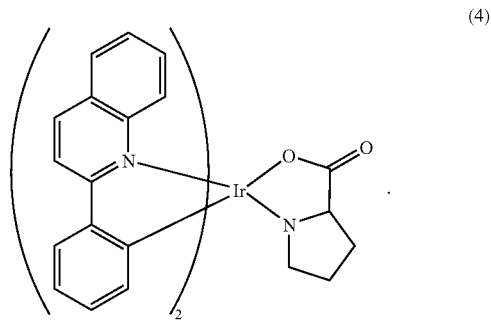

3. The compound of claim 1, having the formula (6):

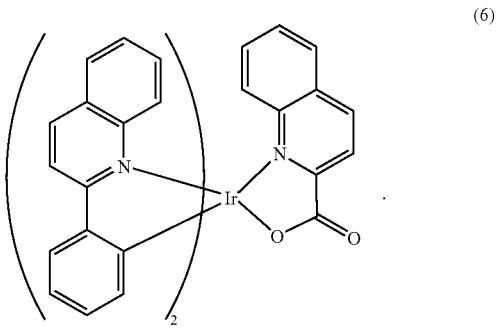

4. The compound of claim 1, having the formulae (7):

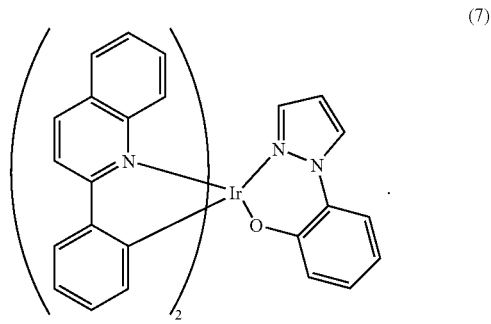

5. An organic electroluminescent device comprising an organic layer between a pair of electrodes, the organic layer containing the compound of said formula (1) according to claim 1.

6. The organic electroluminescent device of claim 5, wherein the organic layer is an emissive layer.

7. An image display device comprising the compound of said formula (1) according to claim 1 as a host material or dopant of an emissive layer of an organic EL device.

* * * * *